US008741679B2

(12) United States Patent
Lai et al.

(10) Patent No.: US 8,741,679 B2
(45) Date of Patent: Jun. 3, 2014

(54) SURFACE TREATMENT METHOD BY USING THE NH₃ PLASMA TREATMENT TO MODIFY THE SENSING THIN-FILM

(75) Inventors: Chao-Sung Lai, Taoyuan County (TW);
Jau-Song Yu, Taoyuan County (TW);
Yu-Sun Chang, New Taipei (TW);
Po-Lung Yang, Taichung (TW);
Tseng-Fu Lu, New Taipei (TW);
Yi-Ting Lin, Miaoli County (TW);
Wen-Yu Chuang, New Taipei (TW);
Ting-Chun Yu, Taoyuan County (TW);
I-Shun Wang, New Taipei (TW);
Jyh-Ping Chen, Taoyuan County (TW);
Chou Chien, Taipei (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 13/466,291

(22) Filed: May 8, 2012

(65) Prior Publication Data
US 2012/0322167 A1    Dec. 20, 2012

(30) Foreign Application Priority Data
Jun. 17, 2011 (TW) ............................. 100121252 A

(51) Int. Cl.
*H01L 21/336*    (2006.01)
*H01L 21/31*     (2006.01)
*G01N 27/414*    (2006.01)
*C12Q 1/00*      (2006.01)
*A61B 5/00*      (2006.01)

(52) U.S. Cl.
USPC ........ 438/49; 204/403.01; 204/416; 257/253; 257/E29.255; 438/1

(58) Field of Classification Search
USPC .......................................................... 438/49
See application file for complete search history.

(56) References Cited

U.S. PATENT DOCUMENTS

| 6,858,524 B2 * | 2/2005 | Haukka et al. ................. 438/585 |
| 2002/0158645 A1 * | 10/2002 | Chou et al. ..................... 324/760 |
| 2004/0150012 A1 * | 8/2004 | Jin et al. ........................ 257/255 |
| 2007/0042609 A1 * | 2/2007 | Senkevich et al. ............ 438/778 |
| 2007/0049053 A1 * | 3/2007 | Mahajani ...................... 438/785 |
| 2008/0186495 A1 * | 8/2008 | Prasad et al. .................. 356/440 |
| 2010/0137143 A1 * | 6/2010 | Rothberg et al. ................ 506/2 |
| 2010/0151479 A1 * | 6/2010 | Toumazou et al. ............... 435/6 |

OTHER PUBLICATIONS

N.F. Starodub, W. Torbicz, D. Pijanowska, V.M. Starodub, M.I. Kanjuk, M. Dawgul, Optimisation methods of enzyme integration with transducers for analysis of irreversible inhibitors, Sensors and Actuators B: Chemical, vol. 58, Issues 1-3, Sep. 21, 1999, pp. 420-426.*
Wang, I-Shun, et al.; Amine Group Formation and Bio-applications on ALD HfO2 with Nitridation by NH3 Plasma; Conference: IEEE International Nano Electronics Conference(INEC); Published Date: Jun. 21-24, 2011; Place: Chang Gung University, Tao-Yuan,Taiwan.

* cited by examiner

*Primary Examiner* — Colleen Matthews
*Assistant Examiner* — Regan J Rundio
(74) *Attorney, Agent, or Firm* — Bacon & Thomas, PLLC

(57) ABSTRACT

The NH₃ plasma treatment by remote plasma is firstly proposed to replace the covalent bonding process during surface modification procedure that for amine bond generation.

1 Claim, 4 Drawing Sheets

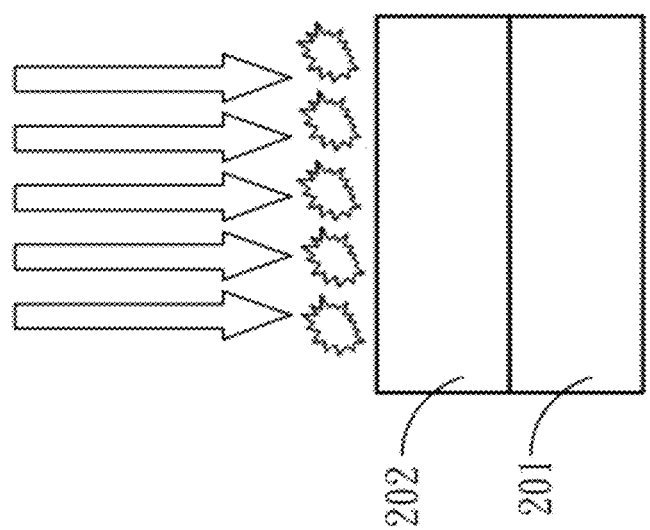
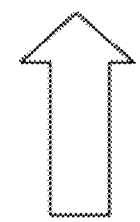
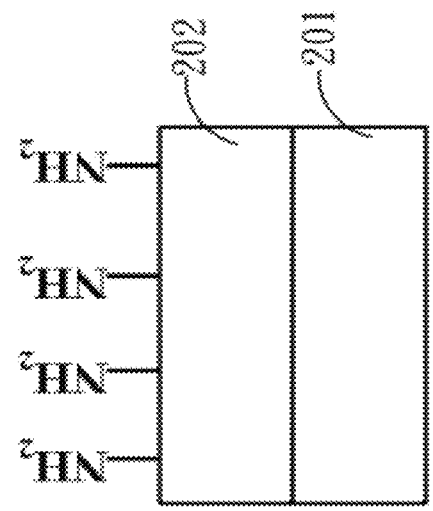
Figure 2A
Figure 2B

SURFACE TREATMENT METHOD BY USING THE $NH_3$ PLASMA TREATMENT TO MODIFY THE SENSING THIN-FILM

BACKGROUND OF THE INVENTION

1. Field of the Invention

The present invention relates to a surface treatment method for the sensing thin-film, particularly to a surface treatment method by using the $NH_3$ plasma treatment to modify the sensing thin-film.

2. Description of the Prior Art

Due to the development of biological sensing technology and biomedical sensing technology is mature recently, the developed technology has been able to be applied in enzyme chip by immobilizing the enzyme on thin-film, and the enzyme can be used to test the electrode for inspecting a large number of samples quickly. There are many successful cases by using the enzyme immobilization to raise the application range of the sensor, such as the glucose sensor, the cholesterol sensor, the lactic acid sensor, and the acetylcroline sensor etc. Thus, it is expected to have an infinite application potential.

The enzyme has been widely applied in various fields of industrial production and inspection at present. The enzyme is one of proteins. The protein is composed of the amino acids arranged in long chain and folded into certain shape. Thus, it has various activity or function. When the amino acid sequence of enzyme is changed, the activity or other properties of enzyme can be changed. In order to increase the stability of enzyme, facilitate the recovery and reuse of enzyme, the enzyme immobilization can be conducted. As for the so-called enzyme immobilization, the enzyme is combined on the carrier by the physical method or the chemical method. The physical confining method can be used to confine the enzyme in a certain area. The chemical bonding method can also be used to bond the enzyme to a certain solid phase object.

However, in numerous enzyme immobilization methods, the adsorption or the entrapment is often used for the physical method. Also, due to the bonding force is relatively weaker, thus the desorption may be caused due to the change of environment and temperature. The covalent-bonding and the cross-linking are often used for the chemical method. The structure change or activity loss of enzyme will be caused due to the strong chemical reaction.

Therefore, in view of the fact that the conventional chemical enzyme immobilization enzyme needs to modify the surface through several reaction steps, such as the change of reagent, or the adjustment of concentration, pH value, reaction temperature, and reaction time etc., the production time and cost will be increased, which is unfavorable for the industrial production process.

Therefore, in order to increase the efficiency of the enzyme immobilization, it is necessary to develop new enzyme immobilization techniques, so as to raise the production efficiency, and reduce the research and development time and relevant manufacturing costs.

SUMMARY OF THE INVENTION

The main purpose of the present invention is to provide a surface treatment method by using the $NH_3$ plasma treatment to modify the sensing thin-film. The plasma process is used to replace the chemical surface modification procedure. The $NH_3$ plasma treatment is applied on the surface of sensing thin-film to form the amino group on the sensing thin-film. The cross-linking agent is then used to immobilize the biological or chemical substance on the surface of sensing thin-film to form the sensing thin-film.

The present invention provides a plasma surface treatment method to carry out the surface amination directly in the process. The cross-linking agent is then combined to shorten the process time and maintain the stability of chemical immobilization.

Compared to the biochemical test result of the conventional sensor, the sensor formed by the present invention has better and more accurate biochemical test result.

Compared to the conventional covalent bonding process, the present invention has the advantages of simplified step and process time saving etc. The purpose of raising process safety and reducing environmental pollution can be achieved.

Therefore, the advantage and spirit of the present invention can be understood further by the following detail description of invention and attached Figures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2A is a diagram illustrating the $NH_3$ plasma treatment of the present invention.

FIG. 2B shows the amino group (—$NH_2$) is formed on the surface of hafnium dioxide sensing membrane after the $NH_3$ plasma treatment.

DESCRIPTION OF THE PREFERRED EMBODIMENT

Figure 1:
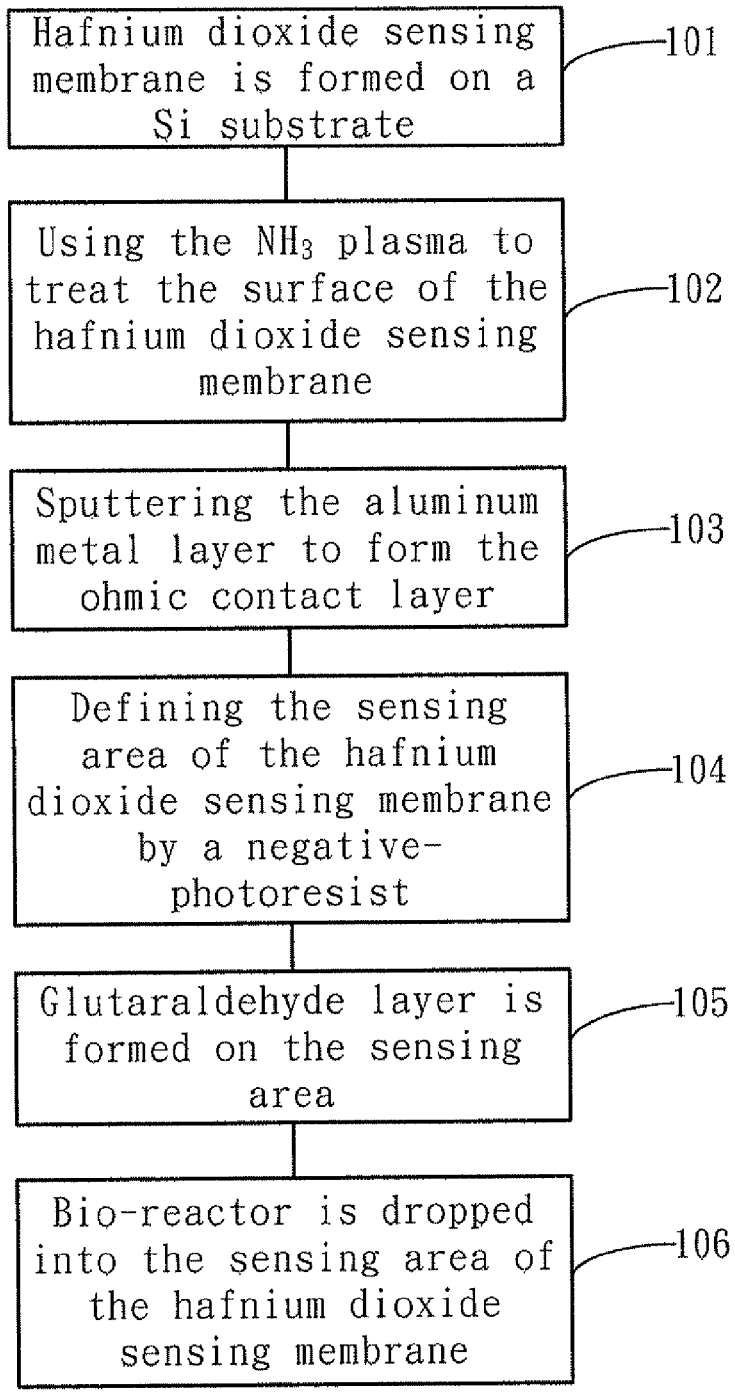
FIG. 1 is a diagram illustrating the flow chart diagram of the present invention.

The present invention provides a surface treatment method by using the $NH_3$ plasma treatment to modify the sensing thin-film. The detailed description of an embodiment is described as follows:

FIG. 1 is a diagram illustrating the flow chart diagram of the present invention. As shown in Step 101 of FIG. 1, the tetrakis(ethylmethylamino) hafnium (TEMAH) is used as the precursor. The Atomic Layer Deposition (ALD) is used and the argon is used as the carrier. The water steam is introduced to provide the oxygen and 15 nm thick hafnium dioxide sensing membrane is formed on a p-type silicon substrate at 200° C.

As shown in Step 102 of FIG. 1, under a constant supply of argon and ammonia, the $NH_3$ plasma is used to treat the surface of the hafnium dioxide sensing membrane at 50W to 200W to form the amino group (—NH2).

FIG. 2A is a diagram illustrating the $NH_3$ plasma treatment of the present invention. The Si substrate 201 and the hafnium dioxide sensing membrane 202 are shown in the FIG. 2A.

FIG. 2B shows the amino group (—$NH_2$) is formed on the surface of hafnium dioxide sensing membrane 202 after the $NH_3$ plasma treatment.

As shown in Step 103 of FIG. 1, a 300 nm thick aluminum metal layer is formed on the back of Si substrate to form an ohmic contact layer.

As shown in Step 104 of FIG. 1, a negative-photoresist of SU8-2005 is used to define the sensing area of hafnium dioxide sensing membrane.

As shown in Step 105 of FIG. 1, the sensing area is immersed in 2.5% Glutaraldehyde solution (i.e. cross-linking agent) to form a Glutaraldehyde layer. The cross-linking agent is used to immobilize the biological or chemical substance on the surface of hafnium dioxide sensing membrane. The Glutaraldehyde is often used as the cross-linking agent. There is an aldehyde group at every end of Glutaraldehyde. The aldehyde group at one end reacts with the amino group formed on the surface of hafnium dioxide sensing membrane, and the aldehyde group at another end reacts with the amino group on the bio-molecule to be immobilized. Thus, the bio-molecule can be immobilized on the surface of hafnium dioxide sensing membrane. The present invention emphasizes the technique for forming the amino acid on surface, the other cross-linking agent may be used to substitute the Glutaraldehyde.

Finally, as shown in Step 106 of FIG. 1, drop the bio-reactor into the sensing area of hafnium dioxide sensing membrane to form the sensing thin-film with the biological and chemical application.

The present invention immobilizes the bio-reactor on the surface of hafnium dioxide sensing membrane. The bio-reactor has biological or chemical reacted molecules, such as the enzyme, antibody, and deoxyribonucleic acid (DNA), to carry on the biological marking in the sensing solution. According to the definition of US Food and Drug Administration (FDA), the biomarker means the substance which can measure the physiological response, disease evolution process, medicine physiological reaction and medicine safety of normal human by any biological assay method. It can be used as the biological feature of the clinical decision, such as the intermediate product of metabolism, gene expression, or protein expression etc. In view of the functionality of biomarker, the biomarker can be divided into eight categories, including the ill biomarker, substituting assessment biomarker, curative or physiological biomarker, physiological mechanism biological, drug effect biomarker, medical objective biomarker, toxicity biomarker, and translating type biomarker etc.

Figure 3:
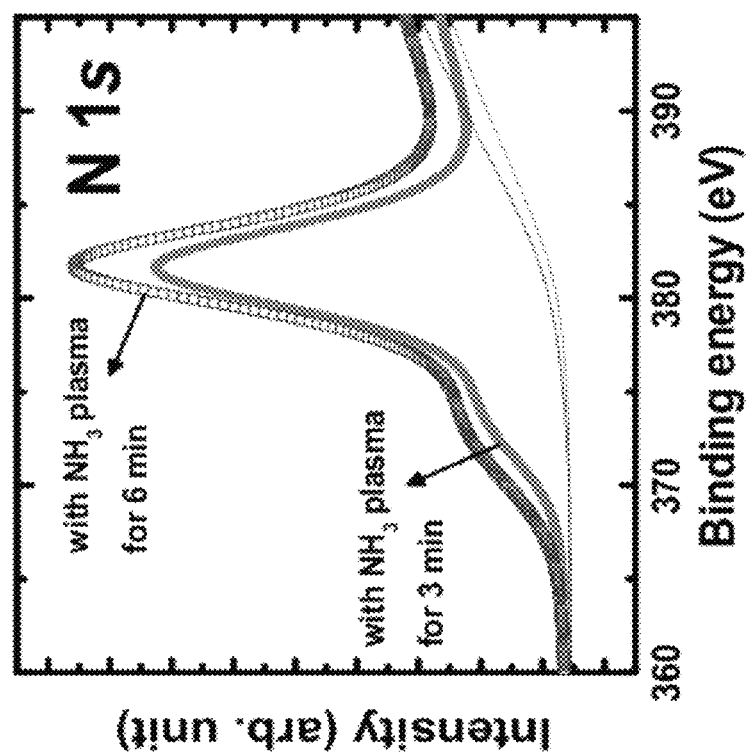
FIG. 3 shows the X-ray photoelectron spectroscopy (XPS) of the present invention.

FIG. 3 shows the X-ray photoelectron spectroscopy (XPS) of the present invention. The abscissa represents the binding energy. The ordinate represents the intensity of photoelectron. It is shown that the $NH_3$ plasma treatment can increase the intensity with respect to the treatment time.

Figure 4:
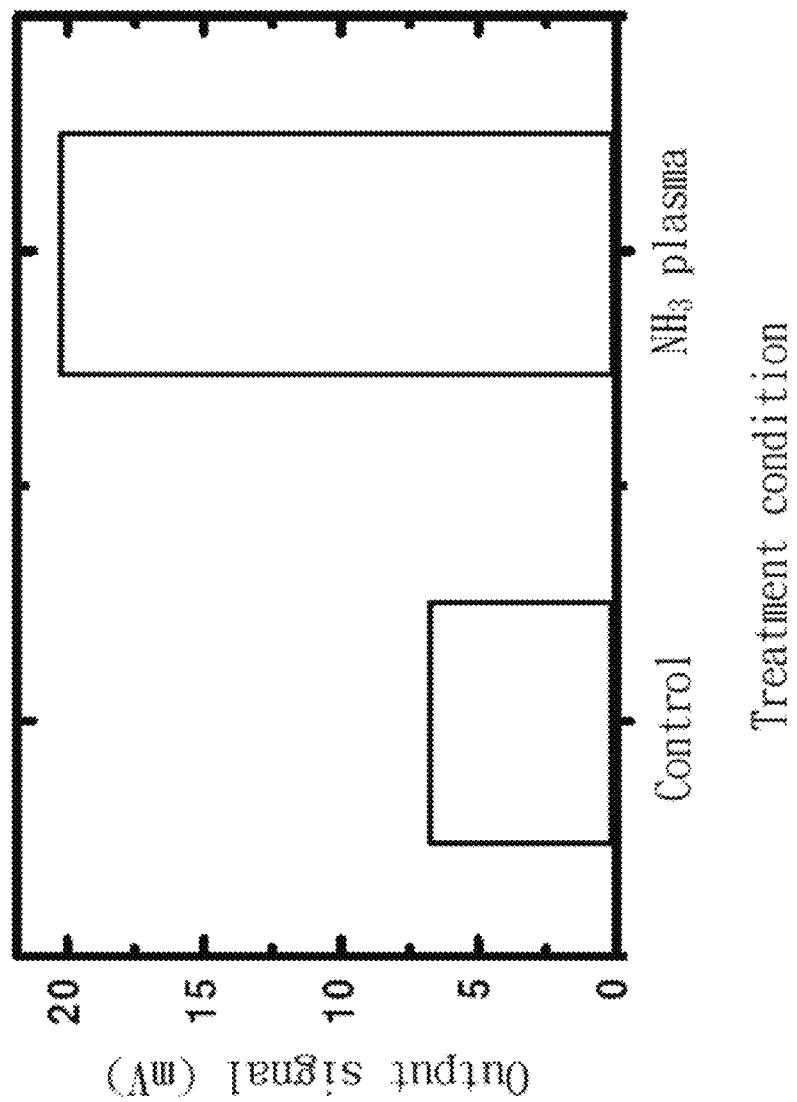
FIG. 4 shows the comparison diagram of the present invention and the conventional inspection response.

FIG. 4 shows the comparison diagram of the present invention and the conventional inspection response. It is shown that the $NH_3$ plasma treatment has better performance than the control group.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A surface treatment method for modifying a sensing thin-film by providing a tetrakis(ethylmethylamino)hafnium as a precursor, using an Atomic Layer Deposition method, using a $NH_3$ plasma method, sputtering an aluminum metal layer, defining a hafnium dioxide sensing membrane area, forming a cross-linking agent layer and dropping a bio-reactor, comprising:

providing a tetrakis(ethylmethylamino)hafnium as a precursor;

using an Atomic Layer Deposition method to form a 15 nm thick hafnium dioxide sensing membrane on a p-type silicon substrate, wherein the Atomic Layer Deposition method comprises using argon as a carries and providing oxygen by introducing water steam, and wherein the Atomic Layer Deposition method is conducted at a temperature of 200°C.;

using a $NH_3$ plasma method to treat a surface of the hafnium dioxide sensing membrane to form an amino group on the hafnium dioxide sensing membrane, wherein the $NH_3$ plasma method comprises providing a constant supply of argon and an ammonia;

sputtering an aluminum metal layer on a back of the silicon substrate to form an ohmic contact layer, wherein the aluminum metal layer is 300 nm thick;

defining a sensing area of the hafnium dioxide sensing membrane by a negative-photoresist;

forming a cross-linking agent layer on the sensing area, wherein the step of forming a cross-linking agent layer on the sensing area comprises using a Glutaraldehyde solution to form a Glutaraldehyde layer on the sensing area; and dropping a bio-reactor into the sensing area of the hafnium dioxide sensing membrane, wherein the bio-reactor is selected from the group consisting of an enzyme, and an antibody.

\* \* \* \* \*